United States Patent
Hoffmann et al.

[11] Patent Number: 5,873,196
[45] Date of Patent: Feb. 23, 1999

[54] IMPLANTABLE DEVICE FOR THE ADMINISTRATION OF ACTIVE SUBSTANCES TO PLANTS

[75] Inventors: Hans-Rainer Hoffmann, Neuwied; Malgorzata Kloczko, Limz; Michael Roreger, Neuwied, all of Germany

[73] Assignee: LTS Lohmann Therapie-Systeme GmbH, Neuwied, Germany

[21] Appl. No.: 836,359

[22] PCT Filed: Oct. 26, 1995

[86] PCT No.: PCT/EP95/04204

§ 371 Date: May 12, 1997

§ 102(e) Date: May 12, 1997

[87] PCT Pub. No.: WO96/15660

PCT Pub. Date: May 30, 1996

[30] Foreign Application Priority Data

Nov. 12, 1994 [DE] Germany .......................... 44 40 528.6

[51] Int. Cl.⁶ .................................................. A01G 29/00
[52] U.S. Cl. ................................................. 47/57.5; 47/1.5
[58] Field of Search ............................ 47/1.5, 62 N, 80, 47/57.5, 48.5

[56] References Cited

U.S. PATENT DOCUMENTS

| | | | |
|---|---|---|---|
| 3,259,677 | 7/1966 | Zwick . | |
| 4,651,468 | 3/1987 | Martinez et al. | 47/80 |
| 4,965,960 | 10/1990 | Moore | 47/1.5 |
| 5,201,925 | 4/1993 | Itzel et al. | 47/58 |
| 5,216,833 | 6/1993 | Longer | 47/1.5 |
| 5,505,021 | 4/1996 | Merving | 47/57.5 |
| 5,689,913 | 11/1997 | Beaudry | 47/1.5 |

FOREIGN PATENT DOCUMENTS

| | | |
|---|---|---|
| 136476 | 10/1985 | European Pat. Off. . |
| 1570608 | 7/1980 | United Kingdom . |

*Primary Examiner*—Michael J. Carone
*Assistant Examiner*—Yvonne R. Abbott
*Attorney, Agent, or Firm*—Wenderoth, Lind & Ponack, L.L.P.

[57] ABSTRACT

In an implantable device for the release of active substances to plants, wherein said device is a ceramic molded article that is interspersed with pores and in which the active substance is distributed in open pores, the pore volume at the time of implantation is dimensioned such that it comprises the total active substance amount to be released, with the kind of the total porosity, its volume, size and scattering as well as the distribution of the pores being determinable within given limits.

18 Claims, No Drawings

IMPLANTABLE DEVICE FOR THE ADMINISTRATION OF ACTIVE SUBSTANCES TO PLANTS

BACKGROUND OF THE INVENTION

The present invention relates to an implantable device for the administration of active substances to plants. Administering active substances to plants by means of implantable devices is known per se and is mentioned in the relevant literature. For example, patent documents JP 58-39602 and AU 84 31497 describe such devices.

The publication JP 58-39602 discloses implantable, swellable active substance systems consisting of a mixture of hydrophilic and water-absorbing polymers. The operating principle of these systems consists in the fact that the release of the active substance is effected as a result of its solubilization and is therefore controlled by the water absorption of the plant. However, this controlling mechanism has the following disadvantage: Since the active substance is released according to the water absorption, the release rates are determined by the hydration state of the plant's tissue cells at the site of application. Previous experience has shown that the degree of cell hydration is subject to great variations, and that the extent of these variations depends on the water balance state of the plant. Extremely low or extremely high water potentials of the plant cells can result either in an interruption of the active substance release or in a rapid release involving an undesired premature exhaustion of the system. A long-term and reliable control of the active substance amount to be released per time unit is not possible with these systems.

The patent AU 843 1497 relates to a release system primarily developed for irrigation and fertilization purposes. It consists of a porous ceramic implant and an external gas or liquid reservoir which are connected with each other. In this case water and active substance are supplied by utilizing the capillary forces of the implant body, the natural transpiration flow of the plant representing the driving power required to transport the active substance carrier liquid. So, both liquid flow and active substance supply to the conductive system of the plant are controlled by the plant itself. For this reason, this system is unsuitable for an exact active substance dosage, rendering the administration of plant protection agents or growth regulators impossible. In forest and horticultural crop protection it is important to adapt the active substance demand to the specific requirements of the respective host-pathogen-relation (time-dependent development of disease and pest attack, extent of the economic damage threshold). The active substance release rate is not the last factor which influences the cost situation in the treatment of a larger stock of plants or trees, for example.

BRIEF SUMMARY OF THE INVENTION

Accordingly, it is the object of the present invention to provide an implantable device for the administration of active substances to plants, wherein the connection of active substance release with the water balance of the plant is limited to a minimum and a control of the active substance release rate is made possible with economic means under avoidance of the above-mentioned difficulties and technical limitations.

This object is achieved with an implantable device having the form according to the features of this invention. Suitable further embodiments of the device are also provided. In this connection, it has surprisingly been found that active substances can be incorporated into the cavity system of porous ceramic bodies and that these are released even into lignified organs of the plant after insertion of the ceramic bodies.

DETAILED DESCRIPTION OF THE INVENTION

The subject matter of the present invention is an implantable device for supplying active substances to plants in the form of a molded article that is interspersed with pores and in which the active substance is distributed in open pores and the pore volume at the time of implantation is dimensioned according to the present invention in such a manner that it comprises the total amount of active substance to be released.

One of the most important characteristics of the device according to the present invention is the type and magnitude of the total porosity, i.e., volume, size and scattering as well as distribution of the pores. Since desired amounts of active substances are to be incorporated into the porous cavity system of the ceramic article, the above-mentioned parameters are decisive for the active substance release. The advantage of the device according to the present invention lies in the utilization of its pore system as a driving and controlling force in the active substance release. This makes it possible to separate the active substance release from the water balance of the plant to a large extent.

Various clay minerals $Al_2O_3 \times 2\ SiO_2 \times 2\ H_2O$ to $Al_2O_3 \times 4\ SiO_2 \times H_2O$ may be used as starting materials for the production of the device according to the present invention. These include, for example, kaolines (kaolinites, allophanes, halloysites), illites (glauconite), smectites (montmorillonite, nontronite, beidellite chlorites), and vermiculites; in general they are present in the mixture. The mentioned clays are characterized by the fact that they swell in moist condition and become plastic, but maintain their form after drying and harden under formation of blown pores during baking at a temperature of between 8000° C. and 2000° C., preferably between 1000° C. and 1200° C. Kaolinites, illites, and halloysites are proposed as particularly suitable for this purpose; they are normally used as ceramic materials in different fields of application. If clays (mechanical mixture of different minerals) are used in the production of the device according to the present invention, their mineral composition and grain structure must be known, because these characteristic values determine the properties and in particular the pore proportion of the ceramic molded article.

The device may also be a ceramic porous molded article that—similar to gas beton—consists of mineral base materials which can be set hydraulically and whose proportion of voids is manufactured by a controllable reaction of chemical components.

The skilled artisan has the following possibilities of influencing the pore structure:

Choice of the clay minerals, variation of the primary particle size, addition of auxiliary agents, and changing the conditions (temperature and time) of the manufacturing method, either by a thermal or a reactive process.

According to the present invention, the starting materials are selected such that the implantable device manufactured thereof is an open-cell structure having a pore volume of about 70 to 95%, in particular 80%. The device according to the present invention has a relatively broad spectrum of pore sizes, it includes values of 0.05 to 5.0 μm. The preferred pore spectrum is the range between 0.1 and 2.0 μm. It is the pore size and pore distribution of the open pores which determines the active substance release rate.

If clay minerals having the same primary particle size are used, a relatively homogeneous pore spectrum (little control of pore size) is achieved in general. The particle size of the used materials can be ascertained by screen classification and by sedimentation in water. The preferred particle size is the range of ≦2 μm. The porosity may be controlled by varying the particle size.

Another possibility of varying the porosity of the device according to the present invention is to use various kinds of additives during its production. As is generally known in the production of ceramic articles, volume is reduced caused by the dehydration. To prevent a possible decrease in the pore space, so-called shortening materials are used. When these substances are added, the eliminated water is replaced by air voids. Suitable supplementary agents include, for example, silicic acid (in the form of quartz or quartzite) or ground fireclay. The use of shortening materials at the same time promotes the physical strength of the end product.

Further product-improving additives which may be used in the production of the device according to the present invention are agents imparting a porous structure. These include organic fibrous materials, such as paper pulp and saw dust, or other combustible materials, such as lignite, limestone, expanded polystyrene and chalk flour. They are incorporated into the mass of raw materials and then burnt out under gasification during the sintering process.

Eventually, another possibility of controlling the porosity in the device according to the present invention are thermal conditions of its production, in particular those of the baking operation. As is generally known, an increase in the baking temperature goes along with a decrease in porosity and an increase in the mechanical properties of ceramic products. The skilled artisan can therefore adapt the conduct of firing during the individual baking stages such that the required porosity properties of the device according to the present invention are achieved. For this purpose the preferred baking temperature is in the range of 950° to 1050° C., and 1000° to 1200° C., respectively.

The device according to the present invention (porous molded article) is impregnated with an aqueous active substance solution in order to load it with active substances. The active substance content in the device can be controlled by the active substance concentration in the solution. Optionally, impregnating with the active substance may be carried out repeatedly to achieve higher active substance contents. According to the present invention 1 to 20%-wt. of active substance may be incorporated into the device, the active substances being present either alone or in mixture with one another.

In principle, any material may be used as active substance which is capable of Influencing processes in the plant or animal organism. Active substances which are systemically or local-systemically active plant protection agents, plant restoratives, growth regulators, nutrients, or other agents for the control of biological processes can be used in the invention. Within the scope of the present invention, plant protection, plant restoratives agents, such as fungicides and insecticides, are preferably used.

Illustrating but not limiting examples of active substances that can be released by means of the device according to the present invention are given in the following:
  fungicides, e.g., benomyl, bromuconazole, bitertanole, etaconazole, flusilazol, furalaxyl, fosetyl-Al, imazalil, metalaxyl, penconazole, propiconazole, thiabendazol, triadimefon, triadimenol, or triforine.
  insecticides, e.g., butocarboxim, dimethoate, fenoxycarb, methamyl, oxamyl, oxydemeton-methyl, pirimicarb, or propoxur.

fertilizers, e.g., superphosphate, Thomas phosphate.

The devices according to the present invention may be obtained as molded pieces of different shape. Particularly preferred are cylindrical, rod- and sphere-shaped molded pieces. They are suitably dimensioned such that they are easy to manipulate by hand. In general the particle size amounts to 2.0 to 100 mm, preferably 5.0 to 50 mm.

A particularly advantageous embodiment of the implant according to the present invention is a device wherein one or several ceramic molded articles are fastened on a rigid plate. The plate consists of a mechanically resistant material which is compatible with plant tissue. Wood is particularly suitable for this purpose. The particular advantage of this embodiment lies in the fact that the plate—by closing the cavity in the plant—forms a protective cover and eliminates, or at least minimizes, the undesired possibility of an active substance exudation, The device according to the present invention is implanted into the plant's shoot axis by inserting it into previously formed cavities (for example drilled holes). The device is particularly suitable for the use in plants having lignified sprouts (shrubs and trees). The present invention will be illustrated in greater detail by the following example:

EXAMPLE 1

25 g of sawdust previously swollen in water was mechanically incorporated (stirred in) in 500 g of a clay mixture consisting of equal parts by weight of Witterschlick blue clay 38/40 and Satzvey blue clay, having a water content of 15% and the following particle size structure:

| Particle size, Diameter in μm | %-wt. |
| --- | --- |
| >63 | 2.0 |
| 63–20 | 1.7 |
| 20–6.3 | 1.7 |
| 6.3–2.0 | 7.2 |
| <2.0 | 88.4 |

Subsequently, the moisture content of the mass so obtained was increased to 40%-wt. under addition of water. In an extruder, the plastic mass so produced was first processed into a "noodle-type article" and then cut into cylindrical molded articles (6 cm ×2 cm ×1 cm). The blank pieces thus obtained were dried in a drying cabinet at 30° C. over a period of 24 hours. Then the dry material was baked in an electrically heated oven (by Naber-Therm) under continuous temperature increase. The residence time of the formed pieces in the main firing temperature range (950° C.) amounted to 1.5 hours. After cooling of the molded pieces, their final dimensions (5.1 cm ×1.7 cm ×0.85 cm) and the total porosity (60%) were determined.

For loading with the active substance, they were impregnated in a 10% Al-fosetyl solution. The active substance amount incorporated in the pore system amounted to 0.2 g/device; this was determined on the basis of the change in weight of the device and the active substance concentration of the solution.

The present invention provides a very simple, easy to handle, and low-priced active substance release system which represents a valuable alternative to conventional techniques, in particular in municipal areas where chemical treatment of trees is very problematic.

We claim:
1. A self-sufficient device for delivering at least one active substance having an effect on plants, which is implantable into a cavity in a plant, said device being formed by a ceramic body having open pores, said pores being impregnated with an active substance solution or an active substance dispersion, wherein the overall pore volume of said device is sufficient for receiving said active substance to be delivered during the period of time the device is implanted into the plant while the pore size and pore distribution are adapted to achieve the desired active substance release rate and is free of external sources of the active substance.

2. The device of claim 1, wherein the ceramic body is a molded article of at least one mineral base material baked at temperatures between 800° C. and 2000°C., the material is a clay material selected from the group consisting of kaolines, illites, smectites, chlorites, and vermiculites.

3. The device of claim 2, wherein the mineral material is baked at a temperature between 1000° C. and 1200° C.

4. The device of claim 2, wherein the kaolines are selected from the group consisting of kaolinites, allophanes and halloysites; the illite is glauconite; and the smectites are selected from the group consisting of montmorillonite, nontronite and beidellite.

5. The device of claim 1, wherein the ceramic body is a molded article of at least one mineral base material which are set hydraulically and have a pore volume caused by chemical reaction.

6. The device of claim 1, wherein the ceramic body comprises additives controlling the pore formation used for the ceramic body production selected from the group consisting of saw dust, paper pulp, lignite, expanded polystyrene, limestone, and chalk flour.

7. The device of claim 1, wherein the ceramic body has an open-cell structure having a pore volume of about 70 to 95%, and that the spectrum of pore size has values of 0.05 to 5.0 $\mu$m.

8. The device of claim 7, wherein the pore volume is 80%.

9. The device of claim 7, wherein the spectrum of pore size is between 0.1 and 2.0 $\mu$m.

10. The device of claim 1, wherein the active substance is systemically or local-systemically active plant protection agents, plant restoratives, growth regulators, or nutrients.

11. The device of claim 1, which further comprises a protective cover in the form of a plate wherein the cover closes the cavity in the plant in which the device is implanted.

12. A method of delivering an active substance to a plant comprising implanting the self sufficient device of claim 1, into a plant.

13. The method of claim 12, wherein the device is implanted into a previously formed cavity in the shoot axis of the plant.

14. A process for the production of the device according to claim 1, wherein in that a porous ceramic body is first made and that the active substance present in a solution or dispersion is incorporated into the pores of the ceramic body by means of impregnation.

15. A self-sufficient implant for delivering at least one active substance having an effect on plants, which is implantable into a cavity in a plant, said implant being formed by a ceramic body having open pores, said pores being impregnated with an active substance solution or an active substance dispersion, wherein the overall pore volume of said implant is sufficient for receiving said active substance to be delivered during the period of time the implant is implanted into the plant while the pore size and pore distribution are adapted to achieve the desired active substance release rate and is free of external sources of the active substance.

16. A method of delivering an active substance to a plant comprising implanting the implant of claim 15, into a plant.

17. The method of claim 16, wherein the implant is implanted into a previously formed cavity in the shoot axis of the plant.

18. A process for the production of the implant according to claim 15, wherein in that a porous ceramic body is first made and that the active substance present in a solution or dispersion is incorporated in to the pores of the ceramic body by means of impregnation.

* * * * *